United States Patent [19]

Noguchi et al.

[11] Patent Number: 5,336,309
[45] Date of Patent: Aug. 9, 1994

[54] FLAKY PIGMENT

[75] Inventors: Tamio Noguchi; Masahiko Yazawa, both of Iwaki, Japan

[73] Assignee: Merck Patent Gesellschaft mit Beschrankter Haftung, Darmstadt, Fed. Rep. of Germany

[21] Appl. No.: 13,867

[22] Filed: Feb. 5, 1993

[30] Foreign Application Priority Data

Feb. 6, 1992 [JP] Japan .................. 4-065470

[51] Int. Cl.$^5$ ............................ C09D 11/00
[52] U.S. Cl. .................. 106/23 C; 106/20 R; 106/23 R; 106/415; 106/417; 106/496; 106/497; 106/498
[58] Field of Search ............... 106/417, 20 R, 23 R, 106/23 C, 415, 496, 497, 498

[56] References Cited

U.S. PATENT DOCUMENTS

| | | | |
|---|---|---|---|
| 4,134,776 | 1/1979 | Rieger et al. | 106/417 |
| 4,574,080 | 3/1986 | Roswall et al. | 424/20 |
| 4,755,229 | 7/1988 | Armanini | 106/413 |
| 4,806,128 | 2/1989 | Figueras | 8/650 |
| 4,915,987 | 4/1990 | Nara et al. | 427/186 |
| 4,954,140 | 9/1990 | Kawashima et al. | 51/295 |
| 4,954,175 | 9/1990 | Ito et al. | 106/417 |
| 5,154,765 | 10/1992 | Armanini | 106/417 |

OTHER PUBLICATIONS

J. A. Hersey, Powder Technology, vol. 11 (1975) pp. 41–44.

*Primary Examiner*—Helene Klemanski
*Assistant Examiner*—Scott L. Hertzog
*Attorney, Agent, or Firm*—Millen, White, Zelano & Branigan

[57] ABSTRACT

The invention provides a flaky pigment comprising particles of a flaky substrate and particles of a pigment or dye, whereby said flaky pigment is in the form of an ordered mixture. The invention also involves preparation of the pigment by a process comprising subjecting said substrate and said pigment or dye to high speed stirring in the absence of a liquid medium.

19 Claims, No Drawings

FLAKY PIGMENT

BACKGROUND OF THE INVENTION

Where pigments and dyes are used in various products as a colorant, it has heretofore been known to be necessary to carry out a pretreatment of the dyes and pigments with an atomizer, roll mill, or sand mill for the purpose of grinding the aggregated pigments and dyes to thereby stabilize their coloration. In such a conventional method, however, selection of the pretreatment conditions is difficult, since the respective pigments and dyes have different cohesive forces. In addition, since some pigments and dyes do not have sufficient dispersion stability, reaggregation of the pulverized particles occurs. Consequently, conventional methods have the drawback of not yielding good coloration.

As a technique for overcoming this drawback of the prior art, Japanese Patent Application Laid-Open No. 62-91565, (U.S. 4,806,128) for example, has proposed a method of obtaining a pigment material with good color by adding a finely powdered flaky substrate to an aqueous solution of a dye, followed by precipitating and depositing dye particles on the surface of the substrate.

Japanese Patent Application Laid-Open No. 63-243168 (U.S. 4,755,229) has proposed formation of a colored mica pigment by precipitating pigment particles on the surfaces of substrates in an aqueous system so as to cover the substrates with the precipitated pigment.

However, since the improved methods in the prior art are so-called wet methods in which treatment is effected in a liquid medium, they require filtration and drying steps so that the cost for manufacturing the product is high. In addition, since dispersion of fine particles of pigments and dyes is often poor, good coloration could not be attained. Thus, the known methods still have drawbacks. Moreover, the pigment or dye particles which have not adhered to the surfaces of the substrates, loosely adhering pigment or dye particles, and excess particles from the pretreatment step would be separated or washed out during the subsequent filtering step or washing step. In this case, sufficient coloration would not be attained in proportion to the amount of the dye or pigment used.

SUMMARY OF THE INVENTION

The present invention has as one object obtaining a method of preparing a flaky pigment as coated with pigment and/or dye particles which may be carried out at low cost, which method is simple and yields a flaky pigment having excellent coloring capacity. The present invention provides a novel, improved method of producing a flaky pigment having a better coloring capacity than any other conventional pigment materials and provides a novel flaky pigment obtained by the method.

The present invention also relates to a pigment having good color and transparency which may be used in cosmetics, top coating paints for cars, plastic colorants, printing inks, paints for domestic electric appliances, paints for building materials and urushi (Japanese lacquer) paints, as well as to a method of preparing same.

The present inventors have found that when flaky substrates and pigment and/or dye particles are subjected to high-speed stirring for a predetermined period of time in the absence of a liquid medium for the purpose of coating the surfaces of the flaky substrates with the pigment and/or dye particles, the flaky substrates and the pigment and/or dye particles form an "ordered mixture" (see *Planning of Fine Particles*, published by the Industrial Search Association, Japan, pages 148–149) so that a flaky pigment having excellent color and dispersibility and excellent adhesion of the pigment and/or dye particles to the flaky substrates is obtained.

In accordance with the present invention, therefore, there is provided a flaky pigment having a mean particle size of from 5–60 $\mu$m, which is based on composite particles forming an ordered mixture, the composite particles being formed by subjecting a mixture composed of a flaky substrate comprising flaky substrates each having an aspect ratio of from 10–120 and a pigment and/or a dye comprising particles having a mean particle size of 5 $\mu$m or less, to high-speed stirring treatment in the absence of a liquid medium.

In general, a particle formed by bonding two or more particles to each other is referred to as a "composite". The above-mentioned mixture of the present invention is a composite of plural particles as formed by such bonding. In such a composite of a powder/powder system, a mixed state where fine particles have adhered to the surfaces of other fine particles is called an "ordered mixture" (see Masumi Koishi, *Planning of Fine Particles*, published by the Industrial Search Association, Japan, or Hersey, *Powder Technology*, 11 (1975) 41–44).

The base to be used in the present invention is a flaky substance which is suitable as a substrate for flaky pigment particles. Examples thereof include metal oxide-coated mica, mica, sericite, kaolin, etc. The flaky substrate to be used in the present invention is composed of particles each preferably having an aspect ratio of from 10–120 and preferably having a mean particle size of from 5–60 $\mu$m.

If the flaky substrate particles have an aspect ratio of less than 10, dispersion of fine particles of the pigment and/or dye with them is not effected sufficiently so that the flaky pigment obtained does not have a maximally desirable coloring capacity. On the contrary, if the particles have an aspect ratio of more than 120, retention of the shape of the substrates is difficult, since their mechanical strength and resistance to stirring energy is insufficient.

The pigment and/or dye particles to be used for coating the flaky substrates in the present invention preferably have a mean particle size of 5 $\mu$m or less. If they have a larger particle size than the defined value, the coloring capacity of the flaky pigment obtained would be poor.

Where the flaky pigment of the present invention is used in cosmetics, examples of the above-mentioned coating pigments include azo pigments, such as Pigment Red 57-1, Pigment Red 3, Pigment Yellow 1, etc.; anthraquinone pigments, such as Vat Blue 6, etc.; indigo pigments, such as Vat Blue 1, etc.; thioindigo pigments, such as Vat Red 1, etc.; and phthalocyanine pigments, such as Pigment Blue 15, etc. Examples of coating dyes include azo dyes, such as Acid Yellow 40, Solvent Yellow 5, etc.; nitroso dyes, such as Acid Green 1, etc.; triphenylmethane dyes, such as Acid Blue 5, etc.; xanthene dyes, such as Acid Red 51, Solvent Red 92, Basic Violet 10, etc.; quinoline dyes, such as Acid Yellow 3, Solvent Yellow 33, etc.; and indigo dyes, such as Acid Green 25, Acid Blue 74, etc.

Where the flaky pigments of the present invention are used in coating paints for cars, higher pigments having excellent light resistance and weather resistance are used as the above-mentioned coating pigments. Examples include azomethine pigments, such as Pigment Yellow 117, etc.; quinophthalone pigments, such as Pigment Yellow 138, etc.; isoindolinone pigments such as Pigment Yellow 139, Pigment Orange 66, Pigment Red 257, etc.; condensed azo pigments, such as Pigment Yellow 128, Pigment Brown 23, etc.; flavanthrone pigments, such as Pigment Yellow 24, etc.; perinone pigments, such as Pigment Orange 43, etc.; quinacridone pigments, such as Pigment Orange 48, Pigment Red 122, Pigment Red 206, Pigment Red 207, Pigment Violet 19, etc.; pyranthrone pigments, such as Pigment Orange 51, Pigment Red 216, Pigment Red 226, etc.; thioindigo pigments, such as Pigment Red 88, etc.; naphthol AS pigments, such as Pigment Red 170, Pigment Red 253, etc.; perylene pigments, such as Pigment Red 179, Pigment Violet 29, Pigment Brown 26, etc.; anthraquinone pigments, such as Pigment Red 168, etc.; dioxazine pigments, such as Pigment Violet 23, etc.; phthalocyanine pigments, such as Pigment Blue 15:1 to 6, etc.; and indanethrene pigments, such as Pigment Blue 60, etc.

Where the flaky pigment of the present invention is used in coating paints for general use, coating paints for coloration of plastics, or printing inks, examples of the above-mentioned coating pigments include azo pigments, such as Pigment Red 3, Pigment Red 5, Pigment Yellow 14, Pigment Yellow 83, Pigment Yellow 95, etc.; phthalocyanine pigments, such as Pigment Blue 15:1 to 6, etc.; threne pigments, such as Vat Yellow 20, Vat Orange 3, Pigment Red 177, Vat Blue 4, etc.; indigo pigments, such as Pigment Red 88, etc.; perinone pigments, such as Pigment Orange 43, etc.; perylene pigments, such as Pigment Red 123, Pigment Red 178, etc.; phthalone pigments, such as Pigment Yellow 138, etc.; dioxazine pigments, such as Pigment Violet 23, etc.; quinacridone pigments, such as Pigment Violet 19, Pigment Red 122, etc.; and isoindolinone pigments, such as Pigment Yellow 109, Pigment Yellow 110, etc.

Where the flaky pigment of the present invention is used in coating paints for general use, coating paints for coloration of plastics, or printing inks, examples of the above-mentioned coating dyes include azo dyes, such as Acid Black 1, Direct Red 28, Direct Green 28, Disperse Blue 79, Basic Red 18, etc; anthraquinone dyes, such as Acid Blue 78, Disperse Blue 60, Vat Blue 4, etc.; indigo dyes, such as Vat Blue 1, Vat Red 1, etc.; phthalocyanine dyes, such as copper phthalocyanine, etc.; xanthene dyes, such as Acid Red 94, etc.; thiazine dyes, such as Basic Blue 9, etc.; and reactive dyes, such as Reactive Red 6, Reactive Yellow 3, Reactive Blue 19, Reactive Black 5, etc.

These pigments and dyes are desirably preground prior to application to flaky substrates for coating thereon.

The energy employed for coating the pigment and/or dye grains on the surfaces of flaky substrates is preferably 290 J or more, preferably 390 J or more, per gram of the substance to be treated.

If the energy used is less than 290 J per gram, the frequency of contact of the particles to each other is low because the energy to be imparted thereto by stirring is insufficient to prevent aggregates of pigment and/or dye particles. Consequently, the flaky pigment formed does not have maximally desirable coloring capacity.

The stirring speed in the step of coating pigment and/or dye particles over the surfaces of flaky substrate particles is preferably 30 m/sec or more, more preferably from 40-70 m/sec, for the rotating speed of the stirring blade.

If the rotating speed is less than 30 m/sec, the frequency of contact of the particles to each other is small, aggregates of pigment and/or dye particles remain, and the flaky pigment to be formed does not have maximally desirable coloring capacity.

The type of the stirring reactor and the stirring system with it are not specifically defined, but a batch system mixer is suitable.

The mixing reactor to be used in preparing the flaky pigment of the present invention should be able to impart an energy of 25 J or more, preferably 33 J or more, per $cm^3$ to the capacity of the reactor chamber and to be equipped with stirrer(s) capable of mixing all of the substances as being treated by convection stirring. In addition, in feeding the substances to be treated into the reactor, it is desirable that a mixture of pigment and/or dye particles and flaky substrates is fed thereinto in an amount of 70% or less, preferably from 20-70%, of the capacity of the reactor vessel.

If the energy amount per $cm^3$ is less than 25 J, the frequency of contact of the particles to each other is small because the energy to be imparted thereto by stirring is insufficient to prevent aggregates of pigment and/or dye particles from remaining, and the flaky pigment to be formed does not have a maximally desirable coloring capacity.

If the amount of the substances fed into the reactor is too small, this small amount would be underloaded compared to the power of the stirrer, causing racing of the stirrer. In this case, the motor, shaft, and bearing of the stirrer would break. On the other hand, if the amount is more than 70%, this large amount would be overloaded compared to the power of the stirrer, causing breakage of the above-mentioned parts of the stirrer; or the coloration of the dye and/or pigment as incorporated would be poor, since sufficient motion could not be imparted to the substances as being treated.

In the present invention, although the mechanism of coating pigment and/or dye particles over the surfaces of flaky substrates by high-speed stirring is not completely understood, it may be considered that the stirring energy of high-speed stirring functions as a collision force, a compression force, a shearing force, and a heat-generating factor to yield the effect of finely pulverizing the pigment and/or dye particles and of fixing the pulverized pigment and/or dye particles on the surfaces of the flaky substrates.

In accordance with the method of the present invention, the stirring energy derived from the high-speed stirring, therefore, acts as a collision force, a compression force, a shearing force, and a heat-generating factor having an excellent effect of finely pulverizing and powdering pigment and/or dye particles and for compositating the resulting pigment and/or dye particles with flaky substrates which are harder than the pigment and/or dye particles. Accordingly, the composite flaky pigment thus formed by the method of the present invention is free from lowering of the coloring capacity, and the method of the present invention avoids the high manufacture costs which are inevitable in the conventional wet method. In accordance with the present invention, therefore, a flaky pigment which has excellent coloring capacity, dispersibility, and adhesiveness among the pigment, dye particles, and the flaky substrates can be produced at a low manufacture cost.

Where the pigment of the present invention is used as a pigment material for cosmetics, it displays excellent effects of improving the color, preventing white blur and improving uniform dispersion of the pigment particles. Where the pigment is used as a pigment material in a top coat paint for cars, it displays excellent effects of improving the color and preventing white blur of the undertone. Where it is used as a pigment material for coloring plastics, it displays excellent effects of improving the color and preventing plate-out. Where it is used as a pigment material in printing inks or in coating paints for general use, it displays excellent effects of improving the color, improving uniform dispersibility, and preventing bleeding.

Without further elaboration, it is believed that one skilled in the art, using the preceding description, can utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited herein, and of corresponding Japanese Application No. 92-65470, filed Feb. 2, 1992, are hereby incorporated by reference.

EXAMPLES

EXAMPLE 1

100 g of a mica having a mean aspect ratio of 10 and a mean particle size of 5 μm and 2.56 g of an organic pigment Red 226 were put in a mixer having a capacity of 1200 ml (high-speed blender mixer manufactured by the Warling Company, the total charge percentage being 30%, and were stirred and blended therein with a stirring energy of 84.2 kJ and a stirring speed of 70 m/sec as a rotating speed, to obtain a pigment having a deep color. By observation with a scanning electron microscope, it was confirmed that the particles of the organic pigment Red 226 uniformly adhered to the surfaces of the particles of the pigment.

The pigment thus obtained had a deep color and had good dispersibility, and adhesion of the organic pigment particles to the substrates was good.

EXAMPLE 2

100 g of a mica having a mean aspect ratio of 80 and a mean particle size of 40 μm and 2.56 g of an organic pigment Red 226 were put into the same mixer as that used in Example 1 (the total charge percentage being 25%) and were stirred and blended therein with a stirring energy of 84.2 kJ and a stirring speed of 70 m/sec as a rotating speed, to obtain a pigment having a deep color. By observation with a scanning electron microscope, it was confirmed that the particles of the organic pigment Red 226 uniformly adhered to the surfaces of the particle of the pigment.

The pigment thus obtained had a deep color and good dispersibility, and adhesion of the organic pigment particles to the substrates was good.

EXAMPLE 3

100 g of a titanium oxide-coated mica having a mean aspect ratio of 44 and a mean particle size of 22 μm and 2.56 g of an organic pigment Red 226 were put into the same mixer as that used in Example 1 (the total charge percentage being 28%) and were stirred and blended therein with a stirring energy of 84.2 kJ and a stirring speed of 70 m/sec as a rotating speed, to obtain a pigment having a deep color. By observation with a scanning electron microscope, it was confirmed that the particles of the organic pigment Red 226 uniformly adhered to the surfaces of the particles of the pigment.

The pigment thus obtained had a deep color and had good dispersibility, and adhesion of the organic pigment to the substrates was good.

EXAMPLE 4

The same process as in Example 3 was repeated, except that the stirring and blending was effected with a stirring energy of 40.1 kJ and a stirring speed of 40 m/sec as a rotating speed, to obtain a pigment having a deep color. By observation with an electron microscope, it was confirmed that the particles of the organic pigment Red 226 uniformly adhered to the surfaces of the particles of the pigment.

The pigment thus obtained had a deep color and had good dispersibility, and adhesion of the organic pigment particles to the substrates was good.

EXAMPLE 5

100 g of a silver pearl luster pigment comprising a titanium oxide-coated mica having a mean aspect ratio of 44 and a mean particle size of 22 μm and 20 g of an organic pigment Red 226 were put into the same mixer as that used in Example 1 (the total charge percentage being 40%) and were stirred and blended therein, with a stirring energy of 84.2 kJ and a stirring speed of 70 m/sec as a rotating speed, to obtain a pigment having a deep color. By observation with a scanning electron microscope, it was confirmed that the particles of the organic pigment Red 226 uniformly adhered to the surfaces of the particles of the pigment.

The pigment thus obtained had a deep color and had good dispersibility, and adhesion of the organic pigment particles to the substrates was good.

EXAMPLE 6

100 g of titanium oxide-coated mica having a mean aspect ratio of 44 and a mean particle size of 22 μm and 2.56 g of an organic pigment Blue 404 were put into the same mixer as that used in Example 1 (the total charge percentage being 28%) and were stirred and blended therein with a stirring energy of 84.2 kJ and a stirring speed of 70 m/sec as a rotating speed, to obtain a pigment having a deep color. By observation with a scanning electron microscope, it was confirmed that the particles of the organic pigment Blue 404 uniformly adhered to the surfaces of the particles of the pigment.

The pigment thus obtained had a deep color and good dispersibility, and adhesion of the organic pigment particles to the substrates was good.

EXAMPLE 7

100 g of a titanium oxide-coated mica having a mean aspect ratio of 44 and a mean particle size of 22 μm and 2.56 g of an organic pigment Yellow 401 were put into the same mixer as that used in Example 1 (the total charge percentage being 28%) and were stirred and blended therein, with a stirring energy of 84.2 kJ and a stirring speed of 70 m/sec as a rotating speed, to obtain a pigment having a deep color. By observation with a scanning electron microscope, it was confirmed that the particles of the organic pigment Yellow 401 uniformly adhered to the surfaces of the particles of the pigment.

The pigment thus obtained had a deep color and had good dispersibility, and adhesion of the organic pigment particles to the substrates was good.

EXAMPLE 8

100 g of a titanium oxide-coated mica having a mean aspect ratio of 44 and a mean particle size of 22 μm and 2.56 g of a phthalocyanine higher organic pigment for top coat paint for cars, G-134 (tradename by Sanyo Dye Company, Japan), were put into the same mixer as that used in Example 1 (the total charge percentage being 28%) and were stirred and blended therein with a stirring energy of 84.2 kJ and a stirring speed of 70 m/sec as a rotating speed, to obtain a pigment having a deep color. By observation with a scanning electron microscope, it was confirmed that the particles of the blue pigment G-314 uniformly adhered to the surfaces of the particles of the pigment.

The pigment thus-obtained had a deep color and had good dispersibility, and adhesion of the organic pigment particles to the substrates was good.

COMPARATIVE EXAMPLE 1

100 g of a kaolin having a mean aspect ratio of 5 and a mean particle size of 2 μm (ASP-170, tradename by Fuji Talc Company, Japan) and 2.56 g of an organic pigment Red 226 were put into the same mixer as that used in Example 1 (the total charge percentage being 40%) and were stirred and blended therein with a stirring energy of 84.2 kJ and a stirring speed of 70 m/sec as a rotating speed. However, the resulting product was found to contain aggregates of the organic pigment particles.

COMPARATIVE EXAMPLE 2

100 g of a titanium oxide-coated mica having a mean aspect ratio of 44 and a mean particle size of 22 μm and 2.56 g of an organic pigment Red 226 were put into the same mixer as that used in Example 1 (the total charge percentage being 28%) and were stirred and blended therein with a stirring energy of 20.7 kJ and a stirring speed of 20 m/sec as a rotating speed. However, the resulting product was found to contain aggregates of the organic pigment particles.

COMPARATIVE EXAMPLE 3

200 g of a titanium oxide-coated mica having a mean aspect ratio of 44 and a mean particle size of 22 μm and 7.18 g of an organic pigment Red 226 were put into the same mixer as that used in Example 1 ( the total charge percentage being 80%) and were stirred and blended therein with a stirring energy of 236 kJ and a stirring speed of 70 m/sec as a rotating speed. However, the resulting product was found to contain aggregates of the organic pigment particles.

COMPARATIVE EXAMPLE 4

400 g of organic pigment Red 226, 550 g of an aqueous potassium hydroxide solution having a concentration of 40° Baumé and 1 L of an aqueous sodium thiosulfate solution having a concentration of 200 g/L were added to 10 L of deionized water having a temperature of 95° C. and stirred therein to prepare a colloidal dispersion of a vat dye. 2000 g of the same silver pearl luster pigment as that used in Example 5 were added and dispersed in the colloidal dispersion, which was then subjected to aerial oxidation, with stirring at 80° C. After 15 minutes, 800 g of 15 wt % hydrogen peroxide were added thereto at a speed of about 20 ml/min and stirred for 10 minutes at 85° C. Afterwards, about 600 g of 35% hydrochloric acid were added thereto at a temperature of 70° C., whereby the reaction system was adjusted to have a pH of 5.0. After 2 hours, the product was taken out by filtration and washed. This was dried at 110° C. for 20 hours and then at 145° C. for 4 hours to obtain a red-colored pigment.

The organic pigment-coated flaky pigment samples obtained in Examples 1–5 and Comparative Examples 1–4 were subjected to the following tests to evaluate their properties, the results of which are shown in Table 1:

(1) Visual Test of Determining Presence or Absence of Aggregates of Organic Pigment Particles 0.5 g of a sample to be tested was dispersed in 4.5 g of VS Medium (tradename by Dainichi Seika Company, Japan), and the resulting dispersion was spread on a coated paper and dried thereon, whereupon the presence or absence of aggregates of organic pigment particles in the dried powder was visually inspected.

(2) Test to Determine Degree of Color of the Organic Pigment

For the powdered sample on the coated paper as prepared in (1), a value (45°/0° measuring angle) was measured by the Hunter system. The higher the a value of the tested sample, the more effectively colored the organic pigment Red 226.

(3) Test to Determine the Adhesion Power of Organic Pigment Particles to Substrates 0.1 g of an organic pigment-coated flaky pigment sample was dispersed in 1.9 g of a liquid paraffin 350S (tradename by Chuoh Chemical Company, Japan), and a shear stress was imparted thereto in a Hoover muller (manufactured by Yoshimitsu Seiki Company, Japan) under the conditions of no load and 50 rotations, whereupon the bleeding condition of the dye before and after the Hoover muller test was visually inspected with an optical microscope.

USE EXAMPLES

The flaky pigment of the present invention can be used as a pigment material in cosmetics, a pigment material in top coat paints for cars, a pigment material for coloration of plastics, a pigment material in printing inks, a pigment material in coating paints for domestic electric appliances, a pigment material in coating paints for building parts, and a pigment material in urushi (Japanese lacquer) paints.

Use Example 1

The following illustrates embodiments of using the flaky pigment of the present invention as a pigment material in cosmetics:

| Lipstick | |
| --- | --- |
| Ozokerite | 5 wt % |

-continued

| Lipstick | |
|---|---|
| Ceresin | 5 wt % |
| Paraffin Wax | 10 wt % |
| Glycerin trioctanoate | 20 wt % |
| Diisostearyl Malate | 42 wt % |
| Octyldodecyl Myristate | 10 wt % |
| Pigment Obtained in Example 3 | 8 wt % |
| Antioxidant, Antiseptic, Perfume | ad lib. |

Using the above-mentioned components, lipsticks were prepared.

| Compact Cake/Eye Shadow | |
|---|---|
| Talc | 38 wt % |
| Mica | 5 wt % |
| Magnesium Stearate | 3 wt % |
| Nylon Powder | 8 wt % |
| Pigment Obtained in Example 3 | 35 wt % |
| Red Iron Oxide | 2 wt % |
| Liquid Paraffin | 5 wt % |
| Isopropyl Myristate | 4 wt % |
| Antioxidant, Antiseptic | ad lib. |

Using the above-mentioned components, compact cake/eye shadow cakes were prepared.

| Nail Lacquer | |
|---|---|
| Nitrocellulose | 15 wt % |
| Alkyd Resin | 12 wt % |
| Butyl Phthalate | 6 wt % |
| Butyl Acetate | 23 wt % |
| Ethyl Acetate | 25 wt % |
| Ethanol | 7 wt % |
| Toluene | 5 wt % |
| Pigment Obtained in Example 3 | 5 wt % |
| Organic Bentonite | 2 wt % |

Using the above-mentioned components, a nail lacquer was prepared.

Use Example 2

Where the flaky pigment of the present invention is used as a pigment material in a top coat paint for cars, it is incorporated into the top coat layer in combination with a carbon black pigment, a metal powder such as aluminum powder, and a pearly pigment containing mica as a substrate.

| (A) Acryl-Melamine Resin | 100 wt. pts. |
|---|---|
| Composition of (A) | |
| Acrydec 47-712 | (70 wt %) |
| Superbeckamine G821-60 | (30 wt %) |
| (B) Pigment Obtained in Example 8 | 20 wt. pts. |
| (C) Acryl-Melamine Resin Thinner | ? |
| Composition of (C) | |
| Ethyl Acetate | (50 wt. pts.) |
| Toluene | (30 wt. pts.) |
| N-butanol | (10 wt. pts.) |
| Solbesso No. 150 | (40 wt. pts.) |

A and B were blended, and C was added to the resulting blend so as to thin it to have a viscosity suitable for spray-coating (from 12-15 seconds with Fordcup No. 4). This was coated on a substrate by spray-coating to form a base coat layer thereon.

Use Example 3

The following illustrates an embodiment of using the flaky pigment of the present invention as a pigment for coloration of a plastic material.

| High Density Polyethylene Resin (pellets) | 100 wt. pts. |
|---|---|
| Pigment Obtained in Example 3 | 1 wt. pt. |
| Magnesium Stearate | 0.1 wt. pt. |
| Zinc Stearate | 0.1 wt. pt. |

Pellets having the composition mentioned above were subjected to injection molding through an injection molding machine.

Use Example 4

The following illustrates an embodiment of using the flaky pigment of the present invention as a pigment material for a printing ink:

| CCST Medium (nitrocellulose resin, manufactured by Toyo Ink Company, Japan) | 40 wt. pts. |
|---|---|
| Pigment Obtained in Example 3 | 8 wt. pts. |

A solvent NC 102 (manufactured by Toyo Ink Company) was added to the above-mentioned composition, which was adjusted to have a viscosity of 20 sec (with Zancup No. 3). The ink prepared was used for printing.

TABLE 1

Characteristics of Organic Pigment Coated Flaky Pigments

| No. | Composition | | | Measured Value of Red Degree (a) by Hunter System | Presence or Absence of Aggregates of Red 226 Particles by Visual Inspection | Evaluation of Adhesive Power of Organic Pigment Particles Hoover muller |
|---|---|---|---|---|---|---|
| | Flaky substrate (g) | Organic Pigment Red 226 (g) | Red 226 Coated Percentage (%) | | | |
| Example 1 | 100 | 2.56 | 2.5 | 39.54 | O | O |
| Example 2 | 100 | 2.56 | 2.5 | 39.74 | O | O |
| Example 3 | 100 | 2.56 | 2.5 | 41.67 | O | O |
| Example 4 | 100 | 2.56 | 2.5 | 38.38 | O | O |
| Example 5 | 100 | 20.0 | 16.7 | 53.79 | O | O |
| Comparative Example 1 | 100 | 2.56 | 2.5 | 30.18 | X | X |
| Comparative Example 2 | 100 | 2.56 | 2.5 | 26.49 | X | X |
| Comparative Example 3 | 280 | 7.18 | 2.5 | 33.76 | X | X |
| Comparative | 2000 | 400 | 16.7 | 35.23 | O | O |

TABLE 1-continued

| | | Characteristics of Organic Pigment Coated Flaky Pigments | | | | |
|---|---|---|---|---|---|---|
| | | Composition | | Measured Value | Presence or Absence of | Evaluation of Adhesive |
| No. | Flaky substrate (g) | Organic Pigment Red 226 (g) | Red 226 Coated Percentage (%) | of Red Degree (a) by Hunter System | Aggregates of Red 226 Particles by Visual Inspection | Power of Organic Pigment Particles Hoover muller |
| Example 4 | | | | | | |

(*) Aggregation of Red 226:
◯: Not aggregated.
X: Aggregated.
Peeling of Red 226:
◯: Not peeled (good adhesion)
X: Peeled (bad adhesion)

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A flaky pigment comprising composite particles of a flaky substrate and particles of a pigment or dye, whereby said flaky pigment is in the form of an ordered mixture of the substrate and the pigment or dye.

2. A flaky pigment according to claim 1, wherein the substrate is in the form of particles having an aspect ratio of 10-120, the pigment or dye is in the form of particles having a mean particle size of 5 μm or less, and the flaky pigment has a mean particle size of 5-60 μm.

3. A flaky pigment according to claim 1, wherein the pigment is an azo pigment, an anthraquinone pigment, an indigo pigment, a thioindigo pigment, or a phthalocyanine pigment.

4. A flaky pigment according to claim 1, wherein the dye is an azo dye, a nitroso dye, a triphenylmethane dye, a xanthene dye, a quinoline dye, or an indigo dye.

5. A flaky pigment according to claim 1, wherein the pigment is an azomethine pigment, a quinophthalone pigment, an isoindoline pigment, a condensed azo pigment, a flavanthrone pigment, a perinone pigment, a quinoacridine pigment, a pyranthrone pigment, a thioindigo pigment, a naphthol AS pigment, a perylene pigment, an anthraquinone pigment, a dioxazine pigment, or an indanethrene pigment.

6. A flaky pigment according to claim 2, prepared by a process comprising subjecting said substrate and said pigment or dye to high speed stirring in the absence of a liquid medium.

7. A flaky pigment according to claim 6, wherein a stirring energy of at least 290 J per gram is imparted to the substrate and dye or pigment particles in a gaseous stream.

8. A flaky pigment according to claim 6, wherein the stirring speed is at least 30 m/sec rotating speed.

9. A flaky pigment according to claim 6, wherein stirring is effected in an apparatus having stirring blades imparting an energy of at least 25 J per $cm^3$ of the apparatus.

10. A flaky pigment according to claim 9, wherein the substrate and pigment or dye is fed into the apparatus in an amount of 70% or less of the apparatus capacity.

11. In a paint, cosmetic, plastic, or ink containing a flaky pigment, the improvement wherein the pigment is one of claim 1.

12. In a paint, cosmetic, plastic, or ink containing a flaky pigment, the improvement wherein the pigment is one of claim 2.

13. In a paint, cosmetic, plastic, or ink containing a flaky pigment, the improvement wherein the pigment is one of claim 6.

14. A flaky pigment according to claim 1, prepared by a process comprising subjecting said substrate and said pigment or dye to high speed stirring in the absence of a liquid medium.

15. A flaky pigment according to claim 2, wherein the dye is an azo dye, a nitroso dye, a triphenylmethane dye, a xanthene dye, a quinoline dye or an indigo dye.

16. A flaky pigment according to claim 2, wherein the pigment is an azomethine pigment, a quinophthalone pigment, an isoindoline pigment, a condensed azo pigment, a flavanthrone pigment, a perinone pigment, a quinoacridine pigment, a pyranthrone pigment, a thioindigo pigment, a naphthol AS pigment, a perylene pigment, an anthraquinone pigment, a dioxazine pigment, or an indanethrene pigment.

17. A flaky pigment according to claim 14, wherein the dye is an azo dye, a nitroso dye, a triphenylmethane dye, a xanthene dye, a quinoline dye or an indigo dye.

18. A flaky pigment according to claim 2, wherein the pigment is an azomethine pigment, a quinophthalone pigment, an isoindoline pigment, a condensed azo pigment, a flavanthrone pigment, a perinone pigment, a quinoacridine pigment, a pyranthrone pigment, a thioindigo pigment, a naphthol AS pigment, a perylene pigment, an anthraquinone pigment, a dioxazine pigment, or an indanethrene pigment.

19. A flaky pigment according to claim 1, wherein the flaky substrate is mica, metal oxide-coated mica, sericite or kaolin.

* * * * *